(12) United States Patent
Murayama

(10) Patent No.: US 10,321,801 B2
(45) Date of Patent: Jun. 18, 2019

(54) HIGH FRAME RATE ENDOSCOPIC DEVICE AND METHODS THEREOF

(71) Applicant: FUJIFILM Corporation, Tokyo (JP)

(72) Inventor: Jin Murayama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 451 days.

(21) Appl. No.: 14/151,533

(22) Filed: Jan. 9, 2014

(65) Prior Publication Data
US 2014/0194686 A1    Jul. 10, 2014

(30) Foreign Application Priority Data

Jan. 10, 2013 (JP) ................................ 2013-002976
Sep. 11, 2013 (JP) ................................ 2013-188163

(51) Int. Cl.
*A61B 1/00* (2006.01)
*A61B 1/05* (2006.01)
*A61B 1/06* (2006.01)

(52) U.S. Cl.
CPC ........ *A61B 1/00009* (2013.01); *A61B 1/0002* (2013.01); *A61B 1/00006* (2013.01); *A61B 1/05* (2013.01); *A61B 1/0638* (2013.01)

(58) Field of Classification Search
CPC ..... A61B 1/05; A61B 1/0638; A61B 1/00006; A61B 1/00009; A61B 1/0002;

(Continued)

(56) References Cited

U.S. PATENT DOCUMENTS 8,817,149 B2 * 8/2014 Goto ................. H01L 27/14667
                                                 348/294
8,879,689 B2 * 11/2014 Ohta .................... A61B 6/4233
                                                 378/108

(Continued)

FOREIGN PATENT DOCUMENTS

JP    2007-166486 A    6/2007
JP    2010-68992 A     4/2010

(Continued)

OTHER PUBLICATIONS

Yang et al., "Design of a Video Image Recorder System for Wireless Capsule Endoscopes Based on DSP", 2007, Publ—Springer Berlin Heidelberg, vol. 14, pp. 4192-4195.*

(Continued)

*Primary Examiner* — Alexandra L Newton
(74) *Attorney, Agent, or Firm* — Birch, Stewart, Kolasch & Birch, LLP

(57) ABSTRACT

An endoscopic device includes: a light source unit configured to repeat for every frame period, an operation of emitting illumination light during a front period and turning off the illumination light during a back period of the frame period; a buffer memory mounted in an endoscopic scope and configured to store image information of a frame image signal output from an image capturing unit; and an information transmitting unit configured to read out the image information of the frame image signal from the buffer memory and transmit the image information to an image processing unit, in which the information transmitting unit reads out the image information of the frame image signal from the buffer memory within the frame period.

13 Claims, 9 Drawing Sheets

(58) Field of Classification Search
CPC ..... A61B 1/0005; A61B 1/045; A61B 1/0646; A61B 5/0084; H04N 5/343; H04N 5/374
USPC .......................................................... 600/109
See application file for complete search history.

(56) References Cited

U.S. PATENT DOCUMENTS

| | | | |
|---|---|---|---|
| 2006/0114986 A1* | 6/2006 | Knapp, II | A61B 1/00103 375/240.01 |
| 2008/0084485 A1* | 4/2008 | Aizawa | H04N 1/00204 348/231.9 |
| 2010/0069713 A1 | 3/2010 | Endo et al. | |
| 2010/0280322 A1* | 11/2010 | Mizuyoshi | A61B 1/0638 600/178 |
| 2011/0285883 A1* | 11/2011 | Goto | H01L 27/14667 348/294 |
| 2012/0133751 A1 | 5/2012 | Sakurai et al. | |
| 2013/0113972 A1* | 5/2013 | Goto | H01L 27/14667 348/308 |
| 2013/0135475 A1* | 5/2013 | Stam | B60Q 1/1423 348/148 |
| 2013/0137926 A1* | 5/2013 | Itai | A61B 1/0005 600/111 |
| 2013/0158349 A1* | 6/2013 | Ashida | A61B 1/00133 600/109 |
| 2013/0313410 A1* | 11/2013 | Goto | H04N 5/3698 250/208.1 |

FOREIGN PATENT DOCUMENTS

| | | |
|---|---|---|
| JP | 2011-30985 A | 2/2011 |
| JP | 2012-115310 A | 6/2012 |
| JP | 2012-239815 A | 12/2012 |
| WO | WO 2012/176561 A1 | 12/2012 |

OTHER PUBLICATIONS

Japanese Office Action, dated Feb. 17, 2015, for Japanese Application No. 2013-188163, along with a partial English translation.
Chinese Office Action and Search Report, dated Mar. 4, 2016, for Chinese Application No. 201410012516.8, with an English translation thereof.
Extended European Search Report dated Jun. 14, 2018, for corresponding EP Application No. 14150479.5.
Japanese Notification of Reasons of Refusal, dated Jan. 31, 2017 for Japanese Application No. 2016-043114, with an English machine translation.

\* cited by examiner

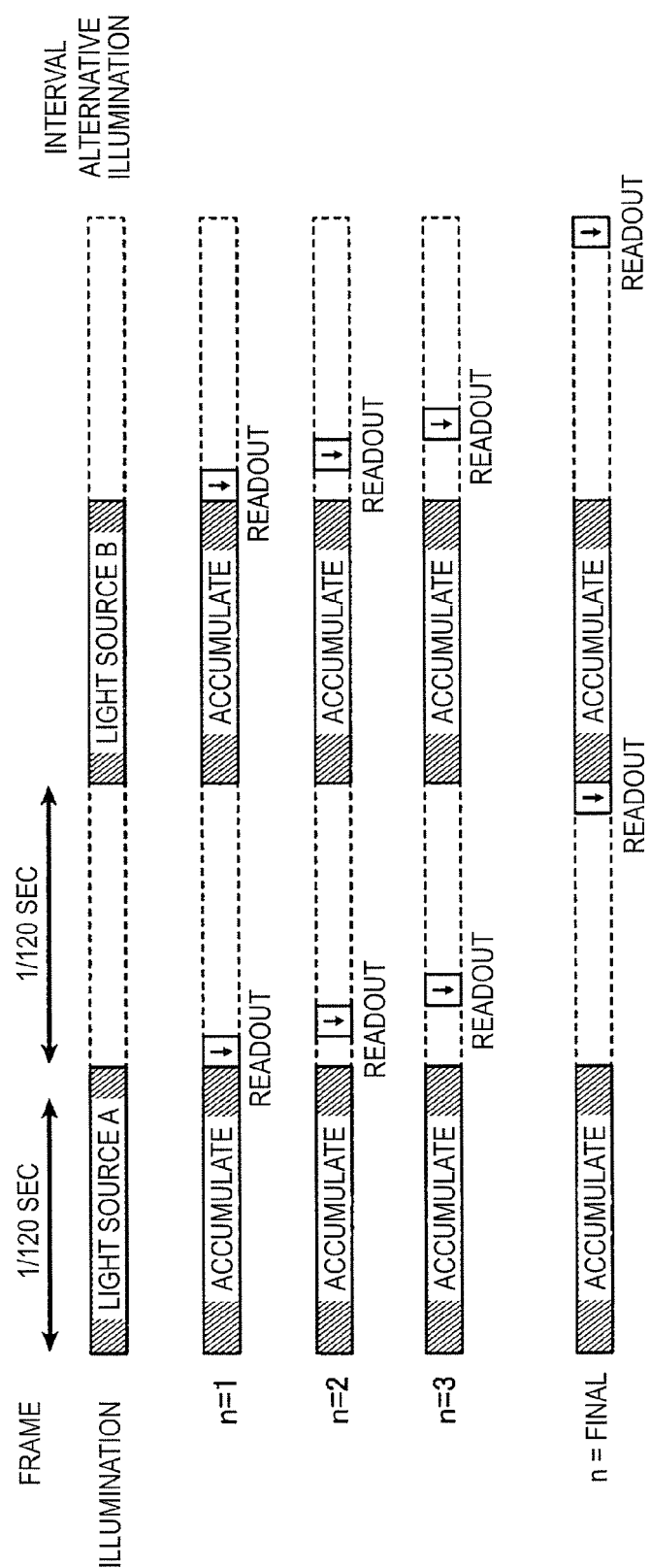

HIGH FRAME RATE ENDOSCOPIC DEVICE AND METHODS THEREOF

CROSS-REFERENCE TO RELATED APPLICATIONS

This application is based on and claims priority under 35 U.S.C. 119 from Japanese Patent Application Nos. 2013-002976 filed on Jan. 10, 2013 and 2013-188163 filed on Sep. 11, 2013, the entire contents of which are incorporated herein by reference.

BACKGROUND

1. Technical Field

The present invention relates to an endoscopic device and an operating method thereof.

2. Related Art

An electronic endoscopic device includes an image capturing unit mounted at a tip portion of an endoscopic scope which is inserted in a body cavity of a subject. An image signal which is captured by the image capturing unit is transmitted to a processor device to which the endoscopic scope is connected, processed and then displayed on a display unit.

The image capturing unit which is used for the endoscopic device is mainly divided into a CCD type and a CMOS type but the CMOS type has been mainly used in recent years. A driving method which reads out the image captured signal to the outside in the CMOS type image capturing unit includes a global shutter method and a rolling shutter method.

The global shutter method concurrently resets all pixels in one screen to start an exposure operation in the CMOS type image capturing unit, that is, starts the accumulation of charges for all pixels in one screen. Therefore, the global shutter method has an advantage in that timings and periods of all pixels (photodiode: PD) from the start of the accumulation of the image capturing unit to the end of the accumulation of the image capturing unit become equal to each other. However, it is required to provide a primary capacity and an FET which transmits the primary capacity in an area of each of the pixels, which may affect the large area of the image capturing unit. Therefore, the configuration may be disadvantageous to mount the image capturing unit in an endoscopic scope with a small diameter.

According to the rolling shutter method, a CMOS type image capturing unit sequentially performs the exposure on at least one scanning line or each pixel so that the scanning lines or the pixels are sequentially reset and the charges start to be accumulated to read out the accumulated charges (also referred to as a focal plane shutter method).

The rolling shutter method is generally used for a digital camera but when the rolling shutter method is applied to the endoscopic device, a problem may occur. The endoscopic scope is inserted in a dark portion such as an inside of the body cavity so that illumination light needs to be irradiated from the tip portion of the scope to capture an image. Pulse light which is flickering light may be used as the illumination light as described in Patent Literature 1 (JP-A-2011-30985). If an on/off timing of the pulse light is not synchronized with a sequential read-out timing of the rolling shutter, a problem may be caused by an amount of illumination light.

FIG. 7 is a diagram illustrating an example of a problem of the rolling shutter method. In the case of the rolling shutter method, even though timings of starting the accumulation of the charges may be deviated in the order of the scanning lines (horizontal pixel row), it is required to irradiate the same amount of light for every scanning line.

The illumination light is pulse modulation driven pulse light. Therefore, pulse widths, the number of pulses, and pulse densities of the driving signals may be controlled to be equal to each other so that total light amounts of the respective scanning lines become the same during the exposure period. However, an amount of irradiated pulse light needs to be dynamically changed in accordance with a distance to a subject or luminance of an image to be observed so that it is difficult to control to uniformly assign the pulse light in the respective scanning lines whose read-out orders are shifted a little bit. If the amount of irradiated pulse light is not controlled to be the same in the respective scanning lines while controlling the irradiation amount to be changed, a luminance irregularity or a stripe pattern is generated in the image to be observed so that a quality of the captured image deteriorates.

FIG. 8 is a diagram illustrating another problem of the rolling shutter method. FIG. 8 illustrates an endoscopic device which alternately uses a plurality of light sources which has different emission colors to irradiate pulse light as an example. In the example illustrated in FIG. 8, an operation of irradiating for $1/60$ second by a light source A twice and an operation of irradiating for $1/60$ second by a light source B twice are alternately repeated. In the rolling shutter type image capturing unit, a timing of starting the accumulation of the charges and a timing of ending the accumulation of the charges are shifted in the order of the scanning lines so that an invalid frame image in which the pulse light irradiation by the light source A and the pulse light irradiation by the light source B are mixed is generated for every frame. The invalid frame image (denoted by "NG" in the drawing) is not used as an observation image of the endoscope so that a valid frame rate which is a ratio of valid frame images (denoted by "OK" in the drawing) is lowered to be half.

Such a problem may be solved by adopting a driving method of FIG. 9. For example, a frame period of $1/60$ second is divided into a front period of $1/120$ second and a back period of $1/120$ second and the accumulation of the charges in each scanning line starts at the same time and the pulse light is irradiated for the first period of $1/120$ second. Then, the accumulated charges of each scanning line may be read out in the order of the scanning lines during the next back period of $1/120$ second.

The driving method illustrated in FIG. 9 may be performed in an image capturing unit with approximately 0.3 million recorded pixels which is currently widely used in the endoscopic device without any problems. However, it is difficult to apply the driving method to a high pixel image capturing unit offering one million pixels or more which may capture an image with a high definition (HD) image quality. This is because in the case of the high pixel image capturing unit offering one million pixels or more, an amount of data which is read out from all pixels is huge so that it is difficult to output all signals of the accumulated charges from the image capturing unit and transmit the signals to a processor device during the back period of $1/120$ of the frame period. Hereinafter, an example that the number of recorded pixels is 1.3 million pixels will be described.

There is a limitation in increasing a transmission rate in order to transmit the image captured signal to a main body of the endoscopic device which is 3 to 4 m apart from the tip portion of the endoscopic scope so that a time to transmit a signal is elongated. Even though the problem of the time to transmit the signal may be solved by increasing the number of signal lines for transmitting the signal to perform parallel transmission, if the number of signal lines is increased, a diameter of an insertion unit of the endoscopic scope in which the signal lines are accommodated is increased. Therefore, the addition of the signal lines may be against the demand for the reduction of the diameter of the insertion unit.

SUMMARY OF INVENTION

The present invention has been made in an effort to provide an endoscopic device which is capable of obtaining a high frame rate observation image at a high quality in an image capturing unit which is mounted in a tip portion of an insertion unit of an endoscopic scope and an operating method thereof.

Illustrative aspects of the present inventions are stated as in the following:

(1) An endoscopic device including an endoscopic scope which irradiates illumination light from a tip of an insertion unit which is inserted in a subject and outputs a frame image signal which is captured by an image capturing unit mounted in the tip of the insertion unit and a processor device which is connected to the endoscopic scope and includes an image processing unit which performs image processing on the frame image signal, the device including: a light source unit configured to repeat for every frame period, an operation of emitting the illumination light during a front period obtained by dividing a frame period of the frame image signal by two and turning off the illumination light during a back period of the frame period; a buffer memory mounted in the endoscopic scope and configured to store image information of the frame image signal output from the image capturing unit; and an information transmitting unit configured to read out the image information of the frame image signal from the buffer memory and transmit the image information to the image processing unit, in which the image capturing unit considers the front period of the frame period as an exposure period and reads out signals of the exposed accumulated charges within the back period to output the signal to the buffer memory as the image information of the frame image signal, and the information transmitting unit reads out the image information of the frame image signal from the buffer memory within the frame period.

(2) An operating method of an endoscopic device including an endoscopic scope which irradiates illumination light from a tip of an insertion unit which is inserted in a subject and outputs a frame image signal which is captured by an image capturing unit mounted in the tip of the insertion unit and a processor device which is connected to the endoscopic scope and includes an image processing unit which performs image processing on the frame image signal, in which a light source unit repeats for every frame period, an operation of irradiating the illumination light onto the subject from the endoscopic scope during a front period obtained by dividing a frame period of the frame image signal by two to turn off the illumination light during a back period of the frame period; the image capturing unit considers the front period of the frame period as an exposure period and reads out signals of the exposed accumulated charges within the back period to output the signal to the buffer memory which is mounted in the endoscopic scope as the image information of the frame image signal, and an information transmitting unit reads out the image information of the frame image signal from the buffer memory within the frame period and transmits the image information to the image processing unit.

According to any one of the aspects of the present invention, information on a frame image signal which is output from an image capturing unit is temporarily stored in a buffer memory so that the image capturing unit starts next exposure. Further, the frame image signal which is stored in the buffer memory is read out within one frame period to a timing of reading out a next frame image signal. Accordingly, it is possible to obtain a high definition image at a high frame rate without deteriorating an image quality.

BRIEF DESCRIPTION OF DRAWINGS

FIG. 9 is an explanatory diagram illustrating a driving method which drives a CMOS image capturing unit of the related art at a high speed in a rolling shutter driving manner.

DESCRIPTION OF EMBODIMENTS

Hereinafter, an embodiment of the present invention will be described in detail with reference to the drawings.

Figure 1:
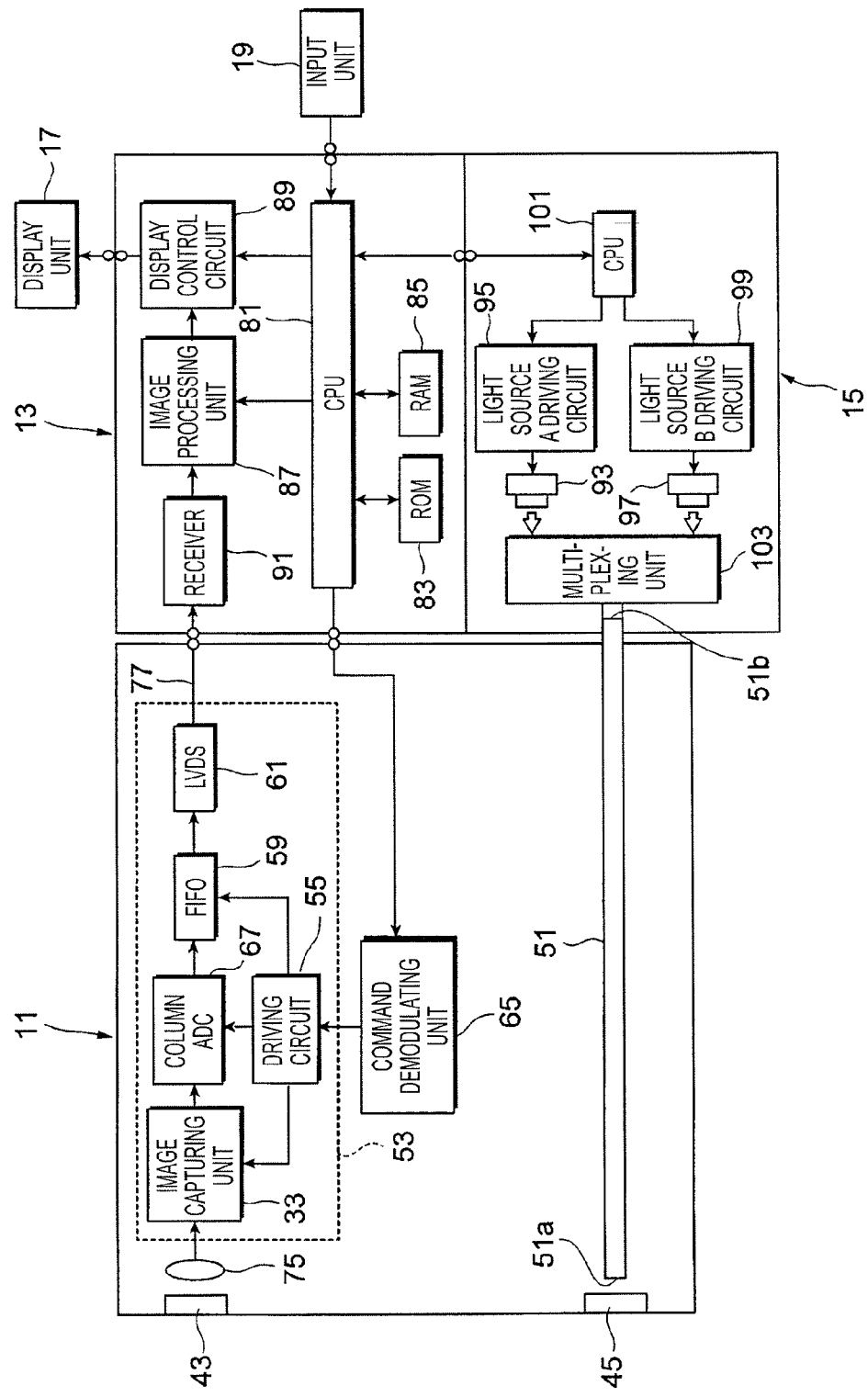
FIG. 1 is a block diagram illustrating an embodiment of the present invention and is a block diagram of an endoscopic device.
Figure 2:
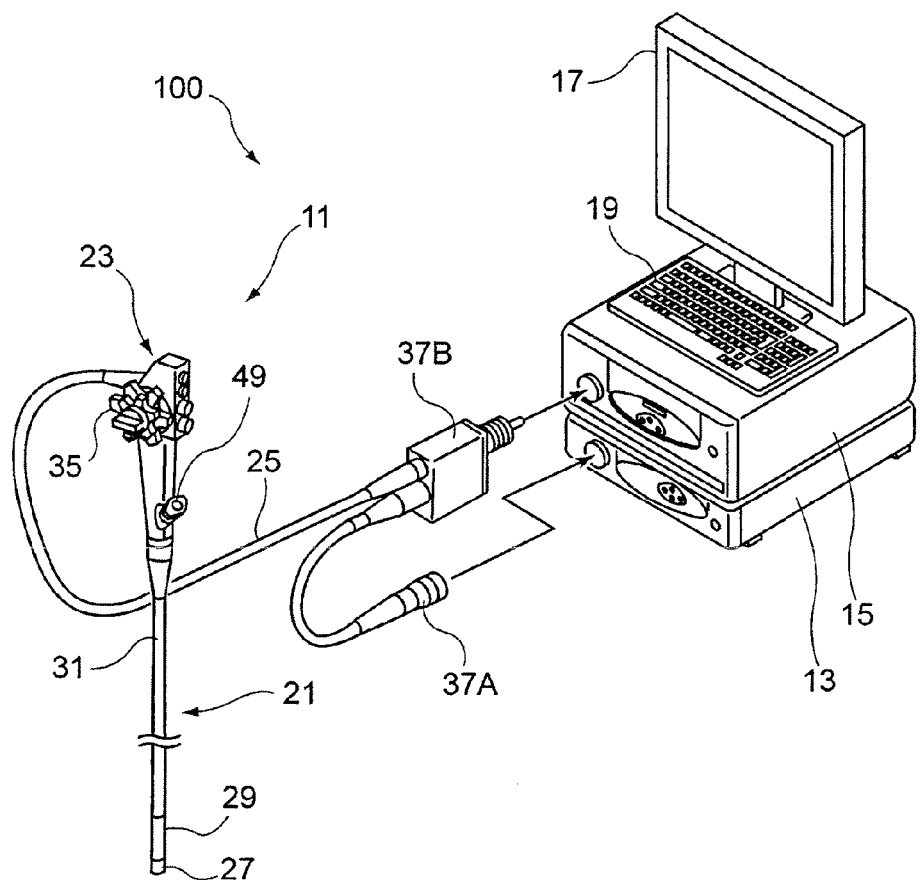
FIG. 2 is an external view as an example of the endoscopic device illustrated in FIG. 1.

FIG. 1 is a diagram illustrating an embodiment of the present invention and is a block diagram of an endoscopic device and FIG. 2 is an external view as an example of the endoscopic device illustrated in FIG. 1.

First, a configuration of an endoscopic device 100 will be described with reference to FIGS. 1 and 2. The endoscopic device 100 includes an endoscopic scope 11, a processor device 13, and a light source device 15. Further, a display unit 17 which displays an observation image and an input unit 19 through which various information is input are connected to the endoscopic device 100.

<Endoscopic Scope>

The endoscopic scope 11 includes a flexible insertion unit 21 which is inserted in a body cavity of a patient (subject), a manipulating unit 23 which is provided next to a base end of the insertion unit 21, and a universal code 25 which is connected to the processor device 13 and the light source device 15, as illustrated in FIG. 2.

The insertion unit 21 includes an endoscopic tip portion 27, a bending portion 29, and a flexible portion 31 which are formed in this order at a tip. The endoscopic tip portion 27 includes a CMOS image capturing unit 33 (see FIG. 1) mounted therein to capture the inside of a body cavity. The bending portion 29 which is disposed at a rear side of the endoscopic tip portion 27 has a bending mechanism to which a plurality of bending pieces is connected. When an angle knob 35 which is provided in the manipulating unit 23 is manipulated, a wire (not illustrated) which is inserted in the insertion unit 21 is extended or pulled to bend the bending unit 29 in up, down, left, and right directions. Accordingly, the endoscopic tip portion 27 is directed to a desired direction in the body cavity.

Connectors 37A and 37B are provided at the base end of the universal code 25. The connector 37A is detachably connected to the processor device 13 and the connector 37B is detachably connected to the light source device 15. The connectors 37A and 37B may be a combination type connector which is integrally connected to the processor device 13 and the light source device 15.

The processor device 13 feeds the power to the endoscopic scope 11 through a signal line which is inserted in and passes through the universal code 25 to control the image capturing unit 33 to be driven, receives an image captured signal which is transmitted through the signal line from the image capturing unit 33, and performs various signal processings on the received image captured signal to convert the image captured signal into image data.

The image data which is converted in the processor device 13 is displayed on the display unit 17 which is connected to the processor device 13 through a cable, such as a liquid crystal monitor, as an observation image. Further, the processor device 13 controls an overall operation of the endoscopic device 100 including the light source device 15. The display unit 17 is not limited to a display device which is provided outside the processor device 13, but may be formed to be various types, and for example, may be integrally formed with the processor device 13 or the endoscopic scope 11.

Figure 3:
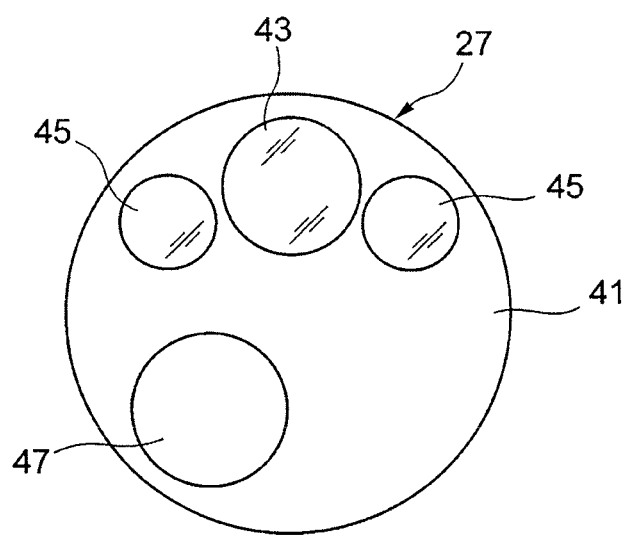
FIG. 3 is a front view illustrating a tip surface of an endoscopic tip portion of an endoscopic scope.

FIG. 3 is a front view illustrating a tip surface 41 of the endoscopic tip portion 27 of the endoscopic scope 11. The tip surface 41 of the endoscopic tip portion 27 includes an observation window 43 through which the subject is observed, illumination windows 45 and 45 through which illumination light is emitted, and a forceps channel 47.

The illumination windows 45 are disposed at both sides of the observation window 43 so as to be substantially symmetrical to each other with the observation window 43 therebetween to irradiate illumination light on a portion to be observed in the body cavity from the light source device 15.

The forceps channel 47 is provided so as to extend along the insertion unit 21 to communicate with a forceps port 49 (see FIG. 2) which is provided in the manipulation unit 23. Various treatment tools in which needles or diathermy knife is disposed at a tip are inserted and pass through the forceps channel 47 so that the tips of the various treatment tools are released from the forceps channel 47 of the endoscopic tip portion 27 into the body cavity.

An emission end 51a of a light guide 51 which guides the illumination light emitted from the light source device 15 is disposed in the illumination window 45 as illustrated in FIG. 1. An optical member such as a lens or an optical diffusion member may be disposed between the emission end 51a of the light guide 51 and the illumination window 45. Further, a fluorescent substance may be disposed at the emission end 51a.

Figure 4:
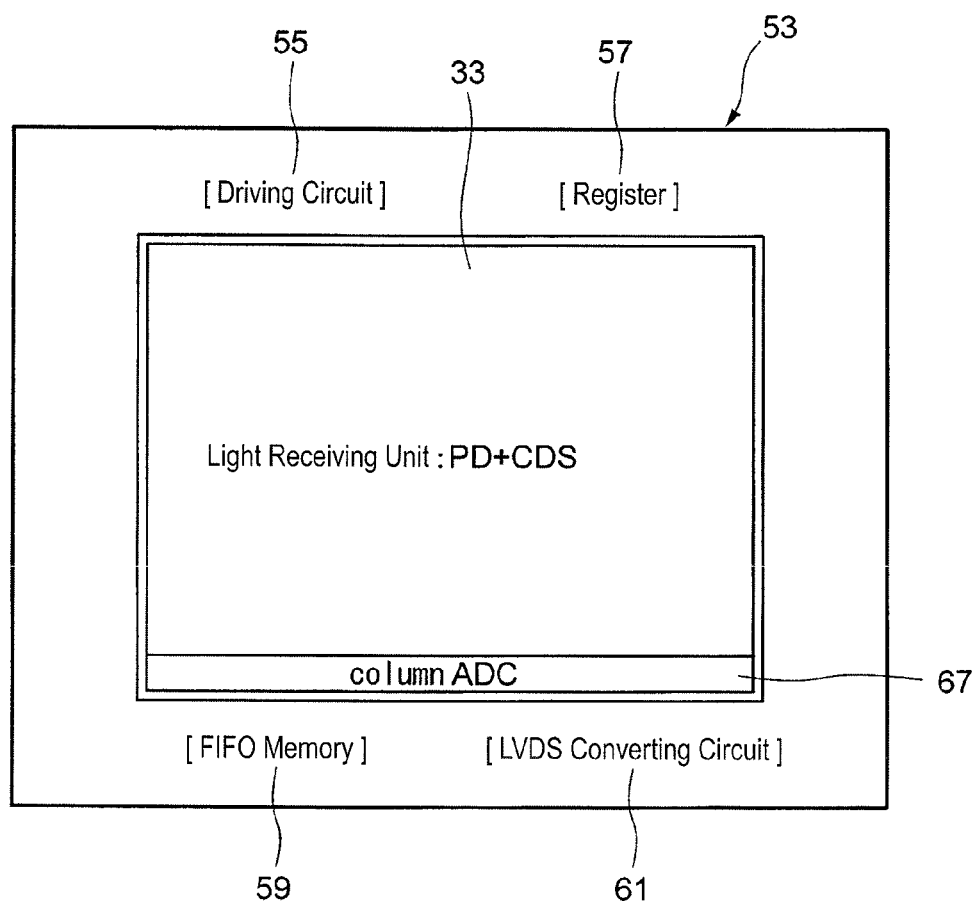
FIG. 4 is a plan view schematically illustrating a surface of a semiconductor element which has an image capturing unit.

FIG. 4 is a plan view schematically illustrating a surface of a semiconductor element which has the image capturing unit 33. An image capturing unit 33 in which a plurality of pixels (light receiving elements, photodiodes (PDs)) is arranged in a two-dimensional array shape is formed at a center region of a rectangular semiconductor element 53. Further, a CDS circuit which performs a correlated double sampling processing is also provided at the center region.

The image capturing unit 33 is a high pixel image capturing unit having 1.3 million recorded pixels or more (approximately vertically one thousand pixels and horizontally 1.3 thousand pixels) and is an image capturing element which may capture a high definition image having an HD image quality. A driving circuit 55 which includes a timing generator (TG), a register 57, a buffer memory 59 (an FIFO memory in this configuration example) which will be described below, and a low voltage differential signaling (LVDS) converting circuit 61 serving as an information transmitting unit are provided in a peripheral region of the image capturing unit 33.

The image capturing unit 33 of this configuration is a one-chip image capturing unit for capturing a color image in which three primary color, that is, red (R), green (G), and blue (B) color filters are laminated on each pixel. The image capturing unit 33 may be a mono color image capturing unit which captures an image by frame-sequentially irradiating the R, G, B color illumination light from the light source which will be described below without mounting a color filter therein. Further, the color filter may adopt any of a combination of R, G, B and white (W) and a combinations of three colors of C, M, and Y or four colors of C, M, Y, and G which are complementary colors in addition to the three primary colors of R, G, and B.

The elements such as the image capturing unit 33, the FIFO memory 59, and the LVDS converting circuit 61 are not formed on one chip, but formed on separate chips to be connected to each other to configure an image capturing unit module. Further, if the FIFO memory 59 and the LVDS converting circuit 61 are disposed in the endoscopic scope 11, the FIFO memory 59 and the LVDS converting circuit 61 may be disposed so as to be spaced apart from the image capturing unit 33.

As illustrated in FIG. 1, the endoscopic scope 11 includes a semiconductor element 53 which includes the image capturing unit 33 and a command demodulating unit 65 which extracts a control signal which controls the endoscopic scope 11. The semiconductor element 53 includes the image capturing unit 33, a column ADC circuit 67, the driving circuit 55, the buffer memory (a FIFO memory which is advantageous in the high speed access in this embodiment) 59, and the low voltage differential signal (LVDS) converting circuit 61.

The image capturing unit 33 outputs a signal of accumulated charges for an i-th scanning line (i is an index indicating first to final lines) to be read out among the scanning lines (pixel row). The output image captured signal is digitalized in the column ADC circuit 67 and then temporarily stored in the FIFO memory 59 as a frame image signal. Thereafter, the frame image signal is sent to the LVDS converting circuit 61 from the FIFO memory 59 in the order of scanning lines.

The driving circuit 55 generates various driving pulses based on the control signal by the command demodulating unit 65 which communicates with the processor device 13 which will be described below. The driving pulses include a driving pulse (a vertical/horizontal scanning pulse or a reset pulse) of the image capturing unit 33, a synchronization pulse for the column ADC circuit 67, and a driving pulse of the FIFO memory 59. The image capturing unit 33 is driven by the driving pulse which is input from the driving circuit 55 to photoelectrically convert an optical image which is focused on a light receiving surface through an objective optical system 75 so as to output the optical image as an image captured signal.

A configuration of a signal readout circuit which reads out the accumulated charges of the photodiodes (PD) of the image capturing unit 33 as an image captured signal is known in the related art and, for example, a general circuit configuration such as a three transistor configuration or four transistor configuration may be applied. One signal readout circuit may be provided for every pixel or one signal readout circuit may be shared by two or four pixels in order to reduce a size of the circuit.

The column ADC circuit 67 is configured by the correlated double sampling (CDS) circuit, an amplifying unit, and an A/D converter (a column AD converter in the embodiment of FIG. 4). The CDS circuit performs a correlated double sampling processing on the image captured signal which is output from the pixel of the image capturing unit 33 to remove a reset noise and an amplification noise which are generated in the image capturing unit 33.

The amplifier amplifies the image captured signal from which the noise is removed by the CDS circuit at a gain (amplifying factor) which is designated by the command demodulating unit 65. The A/D converter converts the image captured signal which is amplified by the amplifier into a digital signal having a predetermined number of bits and outputs the digital signal. The frame image signal which is output from the A/D converter is image information from a first scanning line to a final scanning line and temporarily stored in the FIFO memory 59. The image information of the frame image signal which is stored in the FIFO memory 59 is sequentially read out by the LVDS converting circuit 61 and the readout image information is converted into a low voltage differential signal to be transmitted to the processor device 13 through the signal line 77.

<Processor Device>

As illustrated in FIG. 1, the processor device 13 includes a CPU 81, an ROM 83, an RAM 85, an image processing unit (DSP) 87, a display control circuit 89, and a receiver 91 which receives a frame image signal of the low voltage differential signal transmitted from the endoscopic scope 11 to output the frame image signal to the image processing unit 87.

If the above-mentioned LVDS converting circuit 61 is a two channel subLVDS converting circuit, the receiver 91 restores the signal which is divided into two channels and transmits the signal to the image processing unit 87. In this case, the number of signal lines which are inserted in and pass through the insertion unit 21 of the endoscopic scope 11 is two, which does not increase the diameter of the insertion unit 21.

The CPU 81 controls units in the processor device 13, transfers the control signal to the command demodulating unit 65 of the endoscopic scope 11 or a light source device 15 which will be described below, and controls the entire endoscopic device 100. Various programs for controlling an operation of the processor device 13 or control data are stored in the ROM 83. Further, a program which is executed by the CPU 81 or various data is temporarily stored in the RAM 85.

The image processing unit 87 performs color interpolation, color separation, color balance adjustment, white balance adjustment, gamma correction, image enhancement processing on the image captured signal which is received by the receiver 91 based on the control of the CPU 81 to generate image data.

The image data which is output from the image processing unit 87 is input to the display control circuit 89 and the display control circuit 89 converts the image data which is input from the image processing unit 87 into a signal format in accordance with the display unit 17 to display the converted image data on a screen of the display unit 17.

A mode switching unit which selects or switches an operation mode of the image capturing unit 33 or various manipulating units which accept an instruction input of a user are provided in an input unit 19 of the processor device 13.

<Light Source Device>

The light source device 15 includes a light source A (93), a light source A driving circuit 95, a light source B (97), and a light source B driving circuit 99. The light source device 15 further includes a CPU 101 which is connected to the A light source driving circuit 97 and the light source B driving circuit 99 and a multiplexing unit 103 which combines optical paths of light emitted from the light source A (93) and light emitted from the light source B (97) to form a signal channel optical path.

The Light source A (93) and the light source B (97) have different emission spectra. The CPU 101 communicates with the CPU 81 of the processor device 13 to individually control the light source A (93) and the light source B (97) to be driven through the light source A driving circuit 95 and the light source B diving circuit 99.

The light source B driving circuit 95 performs pulse modulation control on the driving signal of the light source A (93) in accordance with the instruction of the CPU 101 to change an on/off timing and a pulse emission amount of the light emitted from the light source A (93). Further, the light source B driving circuit 99 performs pulse modulation control on the driving signal of the light source B (97) in accordance with the instruction of the CPU 101 to change an on/off timing and a pulse emission amount of the light emitted from the light source B (97).

The multiplexing unit 103 emits the emission light of the light source A (93) to an entrance end 51b of the light guide 51 and emits the emission light of the light source B (97) to the entrance end 51b of the light guide 51. When the emission light of the light source A (93) and the emission light of the light source B (97) are simultaneously emitted, the emission light is multiplexed (mixed) to be emitted to the entrance end 51b of the light guide 51.

A semiconductor light source such as a laser diode (LD) or an LED may be used as the light source A (93) and the light source B (97). Further, a configuration which uses a halogen lamp may be adopted. A type of light source may be appropriately selected depending on an observation target or observation purpose. Further, if the halogen lamp is used, a rotary disk with a light chopper slit is provided on a front surface of the light source and a rotating speed of the rotary disk is controlled to control the illumination light to be on/off.

If the LD whose emission wavelength has a narrow band is used as the light source A (93) and the light source B (97), for example, an LD which emits laser light such as near ultraviolet light, blue light, green light, or red light may be used either alone or in combination. For example, when the near ultraviolet light or blue light is used as the illumination light, a capillary or microscopic structure shape of a superficial layer of a body tissue is enhanced. Further, one of the light source A (93) and the light source B (97) may be a white light source which uses an LD which emits the blue light and a fluorescent substance which is excited and emitted to be green to yellow by the blue laser light to generate white light. Further, the fluorescent substance may be disposed at the emission end of the light guide 51 of the tip portion of the endoscopic scope 11.

In order to detect oxygen saturation in the captured image, an LD whose central wavelength is approximately 405 nm, 445 nm, or 473 nm may be selectively used in accordance with an absorbance for an oxygenated hemoglobin and a reduced hemoglobin. In this case, captured images, which have the light of the respective wavelength as the illumination light, are operated to detect a level of the oxygen saturation (for example, see JP-A-2011-92690).

When the inside of the body cavity is observed using the endoscopic device 100 with the above configuration, the insertion unit 21 of the endoscopic scope 11 is inserted in the body cavity to observe an image in the cavity body which is captured by the image capturing unit 33 through the display unit 17 while illuminating the inside of the body cavity with the pulse illumination light from the light source device 15.

The CPU 81 of the processor device 13 controls a light amount of the illumination light from luminance information of the image captured signal which is output from the image capturing unit 33. For example, in the case of long-distance observation in which a subject which is distant from the endoscopic tip portion is observed, the observation image is dark in many cases so that the amount of the illumination light is controlled to be increased. In contrast, in the case of short-distance observation in which the endoscopic tip portion approaches the subject to observe a magnified image, the observation image is too bright so that the amount of the illumination light is controlled to be reduced.

When the amount of the illumination light is controlled to be increased or reduced, the CPU 81 of the processor device 13 outputs a command to the CPU 101 of the light source device 15 to control the amount of emitted light (a pulse width, the number of pulses, or a pulse density of the driving signal) of the light source A (93) and the light source B (97).

<Image Capturing Order>

The image capturing unit with this configuration is an image capturing unit which has one million or more recorded pixels as described above and obtains a high definition image with an HD image quality. Therefore, the amount of data of the captured image is four times or more of the amount of the data of an image capturing unit having 0.3 million pixels class which is widely used for the endoscope. Therefore, in this configuration, the buffer memory 59 is provided in order to read out the signal having the large amount of data from the image capturing unit 33 without having any problems. Further, the LVDS converting circuit 61 is provided in order to transmit the signal having the large amount of data to the processor device 13.

Figure 5:
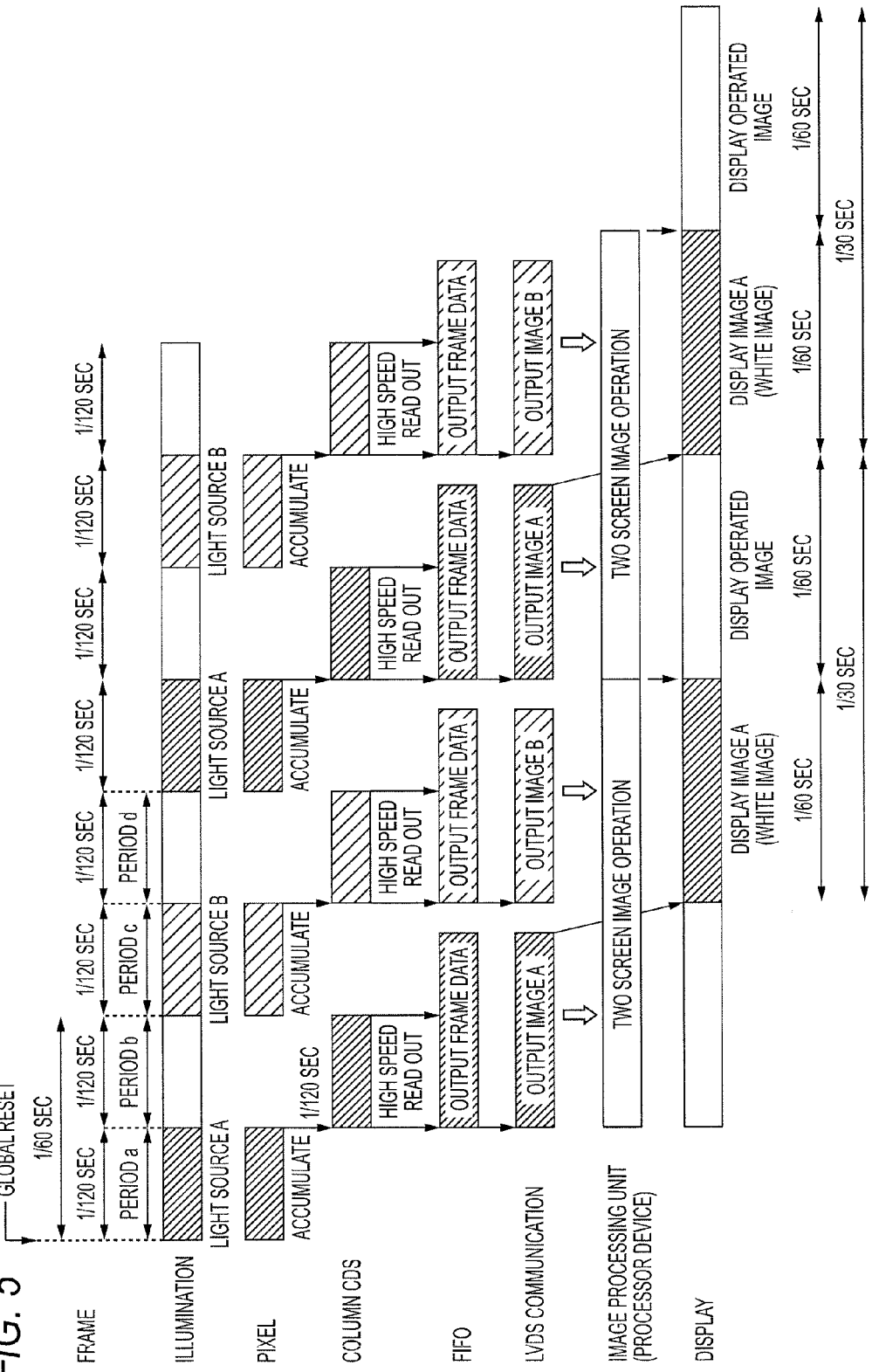
FIG. 5 is a timing chart illustrating a driving method of an endoscopic device.

FIG. 5 is a timing chart illustrating a driving method of the endoscopic device. The endoscopic device 100 with this configuration is configured to capture an image and display an image with a frame rate of 60 frames/second. Here, an example having a frame rate of 60 frames/second will be described.

The light source device 15 alternately turns on the light source A (93) and the light source B (97) which are illustrated in FIG. 1 every 1/60 second which is a frame period. More specifically, the period of 1/60 second which is a frame period is divided by two to be divided into a front period of 1/120 second and a back period of 1/120 second. When it is considered that the front period of the turning on period of the A light source is a period a and the rear period is a period b, only the A light source is turned on only during the front period a and the A light source (and the B light source) is turned off during the rear period b. Similarly, the turning on period of the B light source is divided into a front period c and a back period d, only the B light source is turned on only during the front period c and the B light source (and the A light source) is turned off during the rear period d. The light source is controlled as described above by the CPU 101 which receives the command from the CPU 81 of the processor device 13.

All pixels of the image capturing unit 33 are global-reset in the endoscopic scope 11 and then a pulse of the illumination light of the A light source is irradiated during the period a. By doing this, charges for all pixels of the image capturing unit 33 start to be accumulated by the illumination light of the A light source. Exposure of all pixels of the image capturing unit 33 is completed at the same exposure time by turning off the A light source at an end timing of the period a.

Next, similarly to the driving method illustrated in FIG. 9, the accumulated charges of the scanning lines (horizontal pixel row) are sequentially read out. A signal of the read out accumulated charges is transmitted to the column CDS so that the correlated double sampling processing is performed on the signal and the column AD converting circuit converts the signal into digital data. The converted digital data is temporarily stored in the FIFO memory 59 as a frame image signal.

Referring to FIG. 9, it is described that in the case of the high pixel image capturing unit whose recorded pixels are one million pixels or more, 1/120 second is insufficient as a data transmission time when the image capturing unit reads out the image captured signal and outputs the image captured signal to the processor device 13 (see FIG. 1). With this configuration, a signal of the accumulated charges is output from the image capturing unit 33 to the FIFO memory 59 as a frame image signal within the period b of 1/120 second to completely transmit the frame image signal to the FIFO memory 59.

By doing this, the accumulated charges of all pixels of the image capturing unit 33 are read out before the start of the period c so that the image capturing unit 33 may perform next exposure without any problems. When the frame image data is transmitted to the FIFO memory 59 during the period b, the frame image data is simply stored in the FIFO memory 59 but not transmitted to the processor device 13 so that the transmission may be completed at a high speed.

Next, the LVDS converting circuit 61 reads out the frame image data which is stored in the FIFO memory 59 to convert the frame image data into a low voltage differential signal and transmits the converted signal to the image processing unit 87 of the processor device 13. Here, the transmitted frame image data is referred to as an "image A".

Before completely storing all the frame image data, the frame image data which is stored in the FIFO memory 59 starts to be converted from the image data which has been completely stored into the LVDS and transmitted to the processor device 13. Therefore, the frame image data which is stored in the FIFO memory 59 is desirably completely transmitted to the processor device 13 before a start timing of the period d when next frame image data starts to be stored.

That is, in the semiconductor element 53, the image information of the frame image signal is stored in the FIFO memory 59 and the stored image information of the frame image signal is read out to be transmitted to the processor device 13. The image information is read out within the frame period.

All pixels may be globally reset during every exposure period, that is, after storing the captured image data in the FIFO memory 59 and before performing next exposure of the image capturing unit 33.

As described above, the FIFO memory 59 simultaneously records and reads out the data so that a storage capacitor corresponding to all pixels of the image capturing unit 33 may not be necessarily provided.

For example, if recorded pixels are 1.3 million pixels (horizontal 1300 pixels and vertical 1000 pixels) and a data amount is 10 bits per pixel, a data amount of one frame image is 13 Mbits.

If it is assumed that an amount of signals which are transmitted to the processor device 13 for $\frac{1}{120}$ second is 10 Mbits, 13 Mbits−10 M bits=3 Mbits, is a signal amount which cannot be transmitted for $\frac{1}{120}$ second. That is, 3 Mbits of frame image signals are maintained in the FIFO memory 59 and then transmitted before an end timing of a period c (a period when the charges by the B light source are accumulated) after the period b.

One B (byte) is 8 bits so that 3 Mbits is 375 kB. Therefore, in the case of this configuration, the FIFO memory 59 which has a storage capacity of 375 kB as a minimum necessary may be provided. An FIFO memory having a capacity larger than the above may also be provided.

Next, a transmission rate at which the frame image signal read out from the FIFO memory 59 is transmitted to the processor device 13 will be described.

The captured image data of 10 bits per pixel is obtained by the image capturing unit 33 having 1.3 million recorded pixels so that a size of the image data for one frame is 13 Mbits. An image is transmitted to the processor device 13 at 60 frames/second so that an amount of transmitted data per second is 13 Mbits×60=780 Mbits.

In the communication of subLVDS which is used in this configuration, a data transmission length from the image capturing unit 33 to the processor device 13 is long, for example, 3 to 4 m so that two channels (2 ch) whose operation frequency is 500 MHz are used. That is, in this configuration, data transmission at 1.0 Gbps is allowed and a data transmission rate of 780 Mbps may be stably established.

When the image is transmitted at 120 frames/second, 13 Mbits×120=1560 Mbits and the transmission cannot be performed at the transmission rate of 1.2 Gbits. In this case, for example, if the operation frequency is 800 MHz, the transmission may be allowed.

As described above, the light source device 15 with this configuration performs intermittent lighting control in which an operation of irradiating the pulse light as the illumination light from the endoscopic scope 11 to the subject during a front period which is obtained by dividing the frame period of the frame image signal by two and turning off the light during the back period of the frame period is repeated for every frame period. Further, the image capturing unit 33 is driven by a global shutter method in which global reset is performed to perform an exposure operation, assumes the front period of the frame period as an exposure period, and reads out the exposed signal charge within the back period to output the signal charge to the buffer memory 59 which is mounted in the endoscopic scope 11 as the frame image signal. The stored frame image signal is read out from the buffer memory 59 within the frame period.

The image capturing unit 33 may be driven by a rolling shutter method in which every pixel, every scanning line or every several lines are shifted to be sequentially reset to perform an exposure operation.

As described above, the image data is temporarily stored in the buffer memory so that even when the amount of data to be transmitted is huge, the transmission from the buffer memory 59 to the processor device 13 may be completed using an image capturing unit which increases pixels before the next exposure period of the image capturing unit is completed. Therefore, there is no need to lower the frame rate in order to complete the transmission within the back period of the frame period, so that high speed transmission may be performed.

In the above embodiment, even though the frame period of $\frac{1}{60}$ second is divided into a front period of $\frac{1}{120}$ second and a back period of $\frac{1}{120}$ second and the exposure and the charge accumulation are performed only during the front period and the data is transmitted to the FIFO memory 59 during the back period, but the division type of the front period and the back period is not limited thereto. For example, if an exposure amount is required, $\frac{1}{100}$ second may be a front period and $\frac{1}{150}$ second may be a back period. The CPU 81 of FIG. 1 instructs the CPU 101 to perform this control after obtaining a sufficient capacity of the FIFO memory 59.

<Image Display>

Next, an example of displaying frame image data on the display unit 17 will be described.

Figure 6:
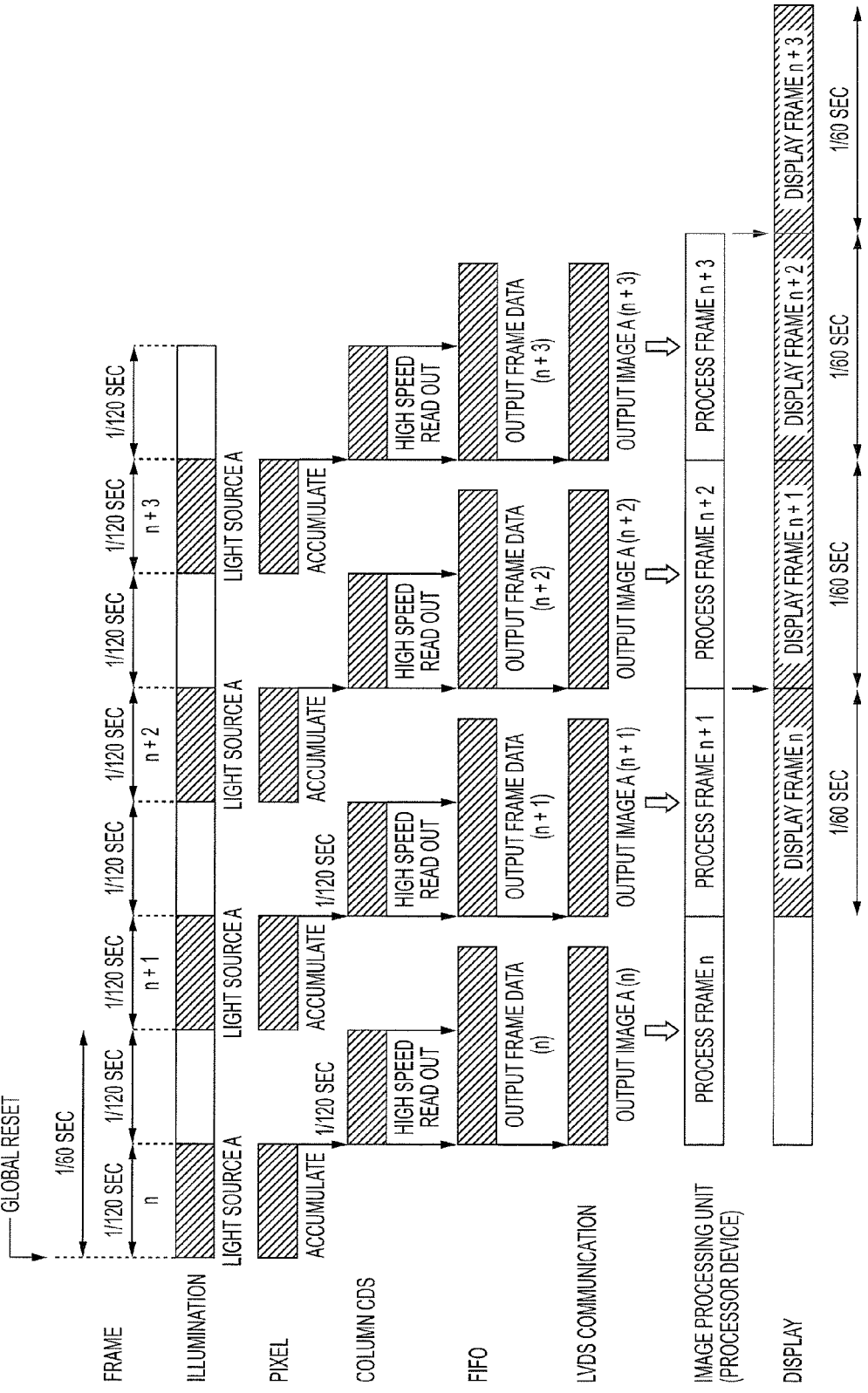
FIG. 6 is a timing chart illustrating a flow of illumination, image-capturing, and an image signal.
Figure 7:
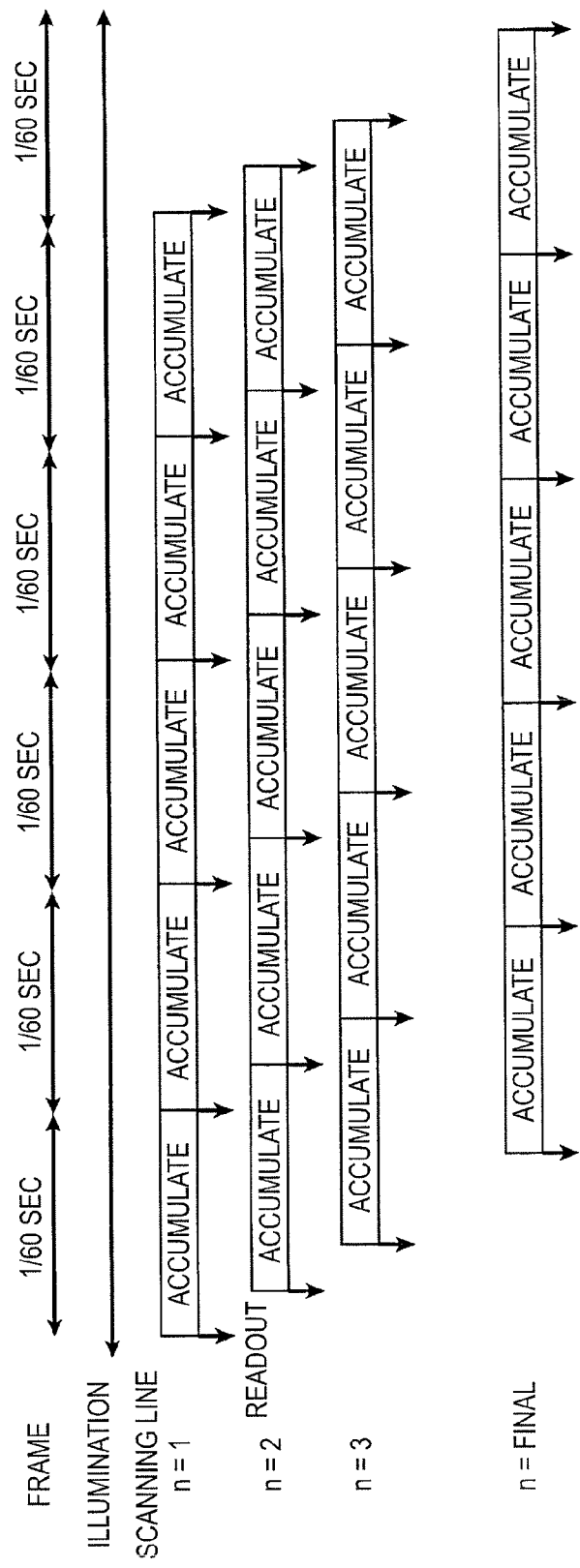
FIG. 7 is an explanatory diagram illustrating an example of a problem of the rolling shutter method of the related art.
Figure 8:
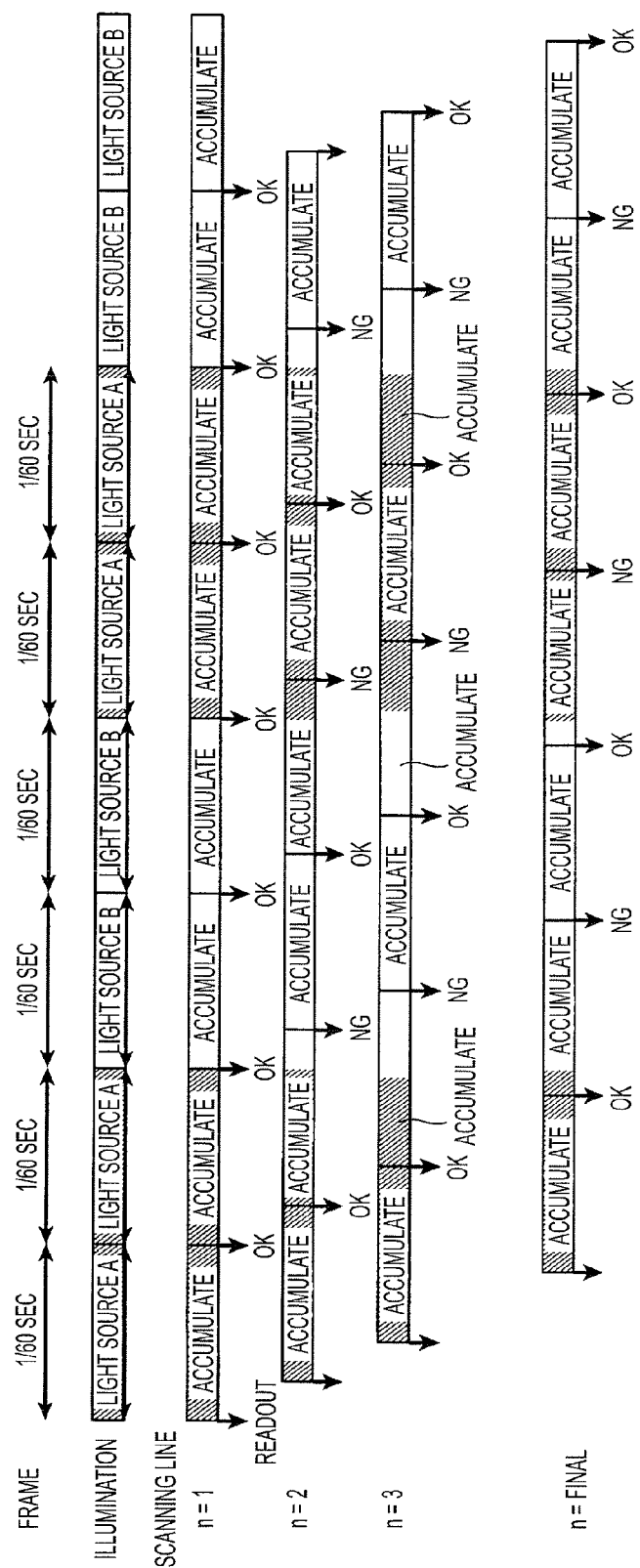
FIG. 8 is an explanatory diagram illustrating another problem of the rolling shutter method of the related art.

FIG. 6 illustrates a flow of illumination, capturing, and an image signal. As described with reference to FIGS. 7 and 8, when an image is captured by a rolling shutter type CMOS sensor using pulse light, pulse heat, and light illumination, a smearing phenomenon such as horizontal stripe is known. As illustrated in FIG. 6, even though the frame is created in the period of $\frac{1}{60}$ second, a sequence in which the illumination and accumulation time is the front period of the frame time and the high speed reading out is performed for the back period is used so that an appropriate simultaneous exposed image which does not depend on the illuminated pulse number and the pulse width may be obtained, similarly to the CCD sensor or the global shutter type CMOS sensor which simultaneously exposes all pixels. The image output becomes a frame image by the image processing unit 87 of FIG. 1 so as to be displayed on the display unit 17 through the display control circuit 89 in the period of $\frac{1}{60}$ second. Here, the delay from the image capturing time to the display time depends on the processing operation of the signal processing unit but is not specifically defined in FIG. 6.

In the control example illustrated in FIG. 5, a white light source is used as the A light source and an LD light source whose central light emitting wavelength is approximately 470 nm which is one of specific wavelengths at which the hemoglobin is absorbed is used as the B light source. An image of the subject which is obtained using the illumination light from the A light source is displayed on the display unit 17 (see FIG. 1) only during $\frac{1}{60}$ second. An operated image which is obtained by operating a frame image obtained by the A light source and a frame image obtained by the B light source in two screens by the image processing unit 87 is displayed during next $\frac{1}{60}$ second. This image is repeatedly displayed for every $\frac{1}{30}$ second (=$\frac{1}{60}$ second+$\frac{1}{60}$ second) so that the operated image is superimposed with the image of the subject by the white light to be displayed on the display unit 17.

The operated image may include an image in which a level of oxygen saturation is represented, an image in which a capillary or microscopic structure shape of a surface of a biological body is enhanced, or a fluorescent observation image.

Even though the A light source and the B light source are alternately turned on in the control example illustrated in FIG. 5, any one of light sources may be used as illumination light to be repeatedly turned on or off.

A C light source is provided so as to prepare three types of light sources and it may also be controlled to sequentially turn on the three types of light sources in the order of the A light source→the B light source→the C light source→the A light source→the B light source→ . . . .

For example, instead of laminating the color filter on each pixel of the image capturing unit 33, a red light source, a green light source, and a blue light source are used as the A light source, the B light source, and the C light source, respectively so that a color image of the subject may be frame-sequentially obtained.

The present invention is not limited to the above-described embodiment but those skilled in the art may combine, change or apply respective components of the embodiment based on the description of the specification and a known technology, which is included in the scope to be protected.

In the above-described configuration, a CMOS type image capturing unit which is formed in the semiconductor element is used, but the image capturing unit is not limited to the CMOS type. The image capturing unit may read out the image captured signal to the outside using an MOS transistor circuit. Further, for example, the image capturing unit may be a photoelectric conversion film laminating image capturing unit as disclosed in JP-B-4887079.

A method which reads out the accumulated charges of the scanning lines is not limited to the global shutter method or the rolling shutter method, but the accumulated charges may be temporarily obtained in a memory and then sequentially extracted from the memory.

The description of embodiments discloses the following:

(1) An endoscopic device including an endoscopic scope which irradiates illumination light from a tip of an insertion unit which is inserted in a subject and outputs a frame image signal which is captured by an image capturing unit mounted in the tip of the insertion unit and a processor device which is connected to the endoscopic scope and includes an image processing unit which performs image processing on the frame image signal, the device including: a light source unit configured to repeat for every frame period, an operation of emitting the illumination light during a front period obtained by dividing a frame period of the frame image signal by two and turning off the illumination light during a back period of the frame period; a buffer memory mounted in the endoscopic scope and configured to store image information of the frame image signal output from the image capturing unit; and an information transmitting unit configured to read out the image information of the frame image signal from the buffer memory and transmit the image information to the image processing unit, in which the image capturing unit considers the front period of the frame period as an exposure period and reads out signals of the exposed accumulated charges within the back period to output the signal to the buffer memory as the image information of the frame image signal, and the information transmitting unit reads out the image information of the frame image signal from the buffer memory within the frame period.

(2) The endoscopic device of (1), in which the image capturing unit is driven by a rolling shutter method.

(3) The endoscopic device of (1) or (2), in which the buffer memory is a memory which is mounted in a semiconductor element including the image capturing unit or connected to the semiconductor element.

(4) The endoscopic device of any one of (1) to (3), in which the buffer memory is an FIFO memory.

(5) The endoscopic device of any one of (1) to (4), in which the buffer memory includes at least a storage capacitor in which a signal amount obtained by subtracting a signal amount which is transmittable during the front period of the frame period from a signal amount of the frame image signal is stored.

(6) The endoscopic device of any one of (1) to (5), in which the information transmitting unit converts the frame image signal into a low voltage differential signal to transmit the converted signal to the image processing unit.

(7) The endoscopic device of any one of (1) to (6), in which the light source unit includes a semiconductor laser element.

(8) The endoscopic device of any one of (1) to (7), in which the light source unit includes an LED element.

(9) The endoscopic device of any one of (1) to (8), in which the light source unit includes a plurality of light sources having different emission colors and the light sources are alternately or sequentially turned on.

(10) The endoscopic device of (9), in which the light source unit emits different color illumination light for every frame period, and the image capturing unit frame-sequentially captures the subject for every illumination light.

(11) The endoscopic device of (10), in which the illumination light includes at least white light and narrow band light of blue to near-ultraviolet light which has a narrower visible wavelength band than the white light.

(12) An operating method of an endoscopic device including an endoscopic scope which irradiates illumination light from a tip of an insertion unit which is inserted in a subject and outputs a frame image signal which is captured by an image capturing unit mounted in the tip of the insertion unit and a processor device which is connected to the endoscopic scope and includes an image processing unit which performs image processing on the frame image signal, in which a light source unit repeats for every frame period, an operation of irradiating the illumination light onto the subject from the endoscopic scope during a front period obtained by dividing a frame period of the frame image signal by two to turn off the illumination light during a back period of the frame period; the image capturing unit considers the front period of the frame period as an exposure period and reads out signals of the exposed accumulated charges within the back period to output the signal to the buffer memory which is mounted in the endoscopic scope as the image information of the frame image signal, and an information transmitting unit reads out the image information of the frame image signal from the buffer memory within the frame period and transmits the image information to the image processing unit.

(13) The operating method of (12), in which the image capturing unit is driven by a rolling shutter method.

INDUSTRIAL APPLICABILITY

The endoscopic device according to the present invention may transmit the large amount of image data with a high quality at a high frame rate so that the present invention may be applied to an endoscopic device in which an image capturing unit for capturing a high definition image is mounted in a tip of an insertion unit of an endoscopic scope.

What is claimed is:

1. An endoscopic device including an endoscopic scope which irradiates illumination light from a tip of an insertion unit which is inserted in a subject and outputs a frame image signal which is captured by an image capturing unit mounted in the tip of the insertion unit and a processor device which is connected to the endoscopic scope and includes an image processing unit which performs image processing on the frame image signal, the endoscopic device comprising:

a light source unit configured to repeat for every frame period, an operation of emitting the illumination light during a front period obtained by dividing a frame period of the frame image signal by two and turning off the illumination light during a back period of the frame period;

a buffer memory mounted in the tip of the insertion unit of the endoscopic scope and configured to store image information of the frame image signal output from the image capturing unit; and an information transmitter mounted in the tip of the insertion unit of the endoscopic scope and configured to read out the image information of the frame image signal from the buffer memory and transmit the image information to the image processing unit, wherein the image capturing unit considers the front period of the frame period as an exposure period and reads out signals of the exposed accumulated charges within the back period to output the signal to the buffer memory as the image information of the frame image signal, and the information transmitter reads out the image information of the frame image signal from the buffer memory and transmits the read out image information to the image processing unit within the frame period.

2. The endoscopic device of claim 1, wherein the image capturing unit is driven by a rolling shutter method.

3. The endoscopic device of claim 1, wherein the buffer memory is a memory which is mounted in a semiconductor element including the image capturing unit or connected to the semiconductor element.

4. The endoscopic device of claim 1, wherein the buffer memory is an FIFO memory.

5. The endoscopic device of claim 1, wherein the buffer memory includes at least a storage capacitor in which a signal amount obtained by subtracting a signal amount which is transmittable during the front period of the frame period from a signal amount of the frame image signal is stored.

6. The endoscopic device of claim 1, wherein the information transmitter converts the frame image signal into a low voltage differential signal to transmit the converted signal to the image processing unit.

7. The endoscopic device of claim 1, wherein the light source unit includes a semiconductor laser element.

8. The endoscopic device of claim 1, wherein the light source unit includes an LED element.

9. The endoscopic device of claim 1, wherein the light source unit includes a plurality of light sources having different emission colors and the light sources are alternately or sequentially turned on.

10. The endoscopic device of claim 9, wherein the light source unit emits different color illumination light for every frame period, and the image capturing unit frame-sequentially captures the subject for every illumination light.

11. The endoscopic device of claim 10, wherein the illumination light includes at least white light and narrow band light of blue to near-ultraviolet light which has a narrower visible wavelength band than the white light.

12. An operating method of an endoscopic device including an endoscopic scope which irradiates illumination light from a tip of an insertion unit which is inserted in a subject and outputs a frame image signal which is captured by an image capturing unit mounted in the tip of the insertion unit and a processor device which is connected to the endoscopic scope and includes an image processing unit which performs image processing on the frame image signal, wherein a light source unit repeats for every frame period, an operation of irradiating the illumination light onto the subject from the endoscopic scope during a front period obtained by dividing a frame period of the frame image signal by two to turn off the illumination light during a back period of the frame period;

the image capturing unit considers the front period of the frame period as an exposure period and reads out signals of the exposed accumulated charges within the back period to output the signal to a buffer memory which is mounted in the tip of the insertion unit of the endoscopic scope as the image information of the frame image signal, and an information transmitter, which is mounted in the tip of the insertion unit of the endoscopic scope, reads out the image information of the frame image signal from the buffer memory and transmits the read out image information to the image processing unit within the frame period.

13. The operating method of claim 12, wherein the image capturing unit is driven by a rolling shutter method.

* * * * *